(12) United States Patent
Sheffer

(10) Patent No.: US 9,555,208 B2
(45) Date of Patent: *Jan. 31, 2017

(54) APPARATUS FOR FLUID TUBE

(71) Applicant: CAREFUSION CORPORATION, San Diego, CA (US)

(72) Inventor: Garrett Austin Sheffer, Towata, NJ (US)

(73) Assignee: VYAIRE MEDICAL CONSUMABLES LLC, Yorba Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/045,173

(22) Filed: Feb. 16, 2016

(65) Prior Publication Data
US 2016/0158479 A1 Jun. 9, 2016

Related U.S. Application Data

(63) Continuation of application No. 14/481,828, filed on Sep. 9, 2014, now Pat. No. 9,283,345, which is a continuation of application No. 13/334,837, filed on Dec. 22, 2011, now Pat. No. 8,826,943.

(51) Int. Cl.
*F16L 11/00* (2006.01)
*A61M 16/08* (2006.01)

(52) U.S. Cl.
CPC .................. *A61M 16/0875* (2013.01)

(58) Field of Classification Search
CPC . F16L 11/11; F01N 2470/12; B29L 2031/703; B29L 2023/18; B29D 23/18; A47L 9/244
USPC ................. 138/121, 122, 118, 119, 115, 116
See application file for complete search history.

(56) References Cited

U.S. PATENT DOCUMENTS

| | | | |
|---|---|---|---|
| 3,678,175 A | 7/1972 | Appiani et al. |
| 3,878,867 A | 4/1975 | Dirks |
| 5,121,746 A | 6/1992 | Sikora |
| 5,746,255 A | 5/1998 | Walsh et al. |
| 5,901,705 A | 5/1999 | Leagre |
| 5,996,639 A | 12/1999 | Gans et al. |
| 6,394,142 B1 | 5/2002 | Woelfel et al. |
| 6,450,205 B1 | 9/2002 | Check |
| 7,178,521 B2 | 2/2007 | Burrow et al. |

(Continued)

FOREIGN PATENT DOCUMENTS

| | | |
|---|---|---|
| CN | 101396576 A | 4/2009 |
| CN | 201359461 Y | 12/2009 |
| CN | 103857434 A | 6/2014 |

OTHER PUBLICATIONS

Chinese First Office Action for Application No. 201210561276.8, dated Dec. 2, 2015, 15 pages.

(Continued)

*Primary Examiner* — Patrick F Brinson
(74) *Attorney, Agent, or Firm* — McDermott Will & Emery LLP

(57) ABSTRACT

A fluid tube is disclosed herein. The breathing circuit tube has a wall which comprises a hollow geometry. The wall defines a passageway with a central longitudinal axis therethrough. The wall is expandable and contractible to adjust a diameter and a length of the passageway. The wall includes one or more corrugations that expand and contract to adjust the diameter and length of the passageway. The corrugations extend between terminal end portions of the wall.

20 Claims, 6 Drawing Sheets

(56) References Cited

U.S. PATENT DOCUMENTS

| | | |
|---|---|---|
| 7,261,105 B2 | 8/2007 | Fukunaga et al. |
| 7,854,264 B2 | 12/2010 | Mandrou et al. |
| 7,921,882 B2 | 4/2011 | Gebhardt |
| 8,291,941 B1 | 10/2012 | Berardi |
| 2002/0036019 A1 | 3/2002 | Woelfel et al. |
| 2009/0133880 A1 | 5/2009 | Mandrou et al. |
| 2012/0036718 A1 | 2/2012 | Stroup, Sr. et al. |

OTHER PUBLICATIONS

Chinese Second Office Action for Application No. 201210561276.8, dated Aug. 12, 2016, 10 pages excluding translation.

APPARATUS FOR FLUID TUBE

CROSS-REFERENCE TO RELATED APPLICATION

This application is a continuation application of U.S. patent application Ser. No. 14/481,828, entitled "APPARATUS FOR FLUID TUBE," filed Sep. 9, 2014 which is a continuation of U.S. Pat. No. 8,826,943, entitled "APPARATUS FOR FLUID TUBE," filed Dec. 22, 2011, the contents of which are incorporated herein by reference and for all purposes.

BACKGROUND OF THE INVENTION

The subject matter disclosed herein relates to a fluid tube such as that commonly used in respiratory care or in an anesthesia environment.

Anesthetic and respirator breathing devices commonly include a breathing circuit to direct gas flow to and away from the patient. At least one tube connects the anesthesia or respiratory device to either the patient face mask or the endo-tracheal tube at the patient end. Tubes of varying length and diameter are used to achieve specific flow resistance.

One problem with conventional respiratory tubing is that health care providers must stock a supply of tubes in multiple diameters to treat a spectrum of patients and conditions. Supplying tubes in multiple diameters also results in excess part numbers, crowded and cluttered hospital rooms, and an increased cost.

BRIEF DESCRIPTION OF THE INVENTION

The above-mentioned shortcomings, disadvantages and problems are addressed herein which will be understood by reading and understanding the following specification.

In an embodiment a fluid tube has a first terminal end portion, a second terminal end portion, and a wall which extends between the first terminal end portion and the second terminal end portion. The wall comprises a hollow geometry defining a passageway with a central longitudinal axis therethrough. The wall further defines one or more expandable corrugations spaced radially around and parallel to the central axis.

In another embodiment, a fluid tube has a first terminal end portion, a second terminal end portion, and a generally cylindrical wall extending between the first terminal end portion and the second terminal end portion. The cylindrical wall comprises a hollow geometry defining a passageway, and the wall defines one or more expandable and contractible corrugations. The expansion and contraction of the corrugations adjusts a diameter of the cylindrical wall.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
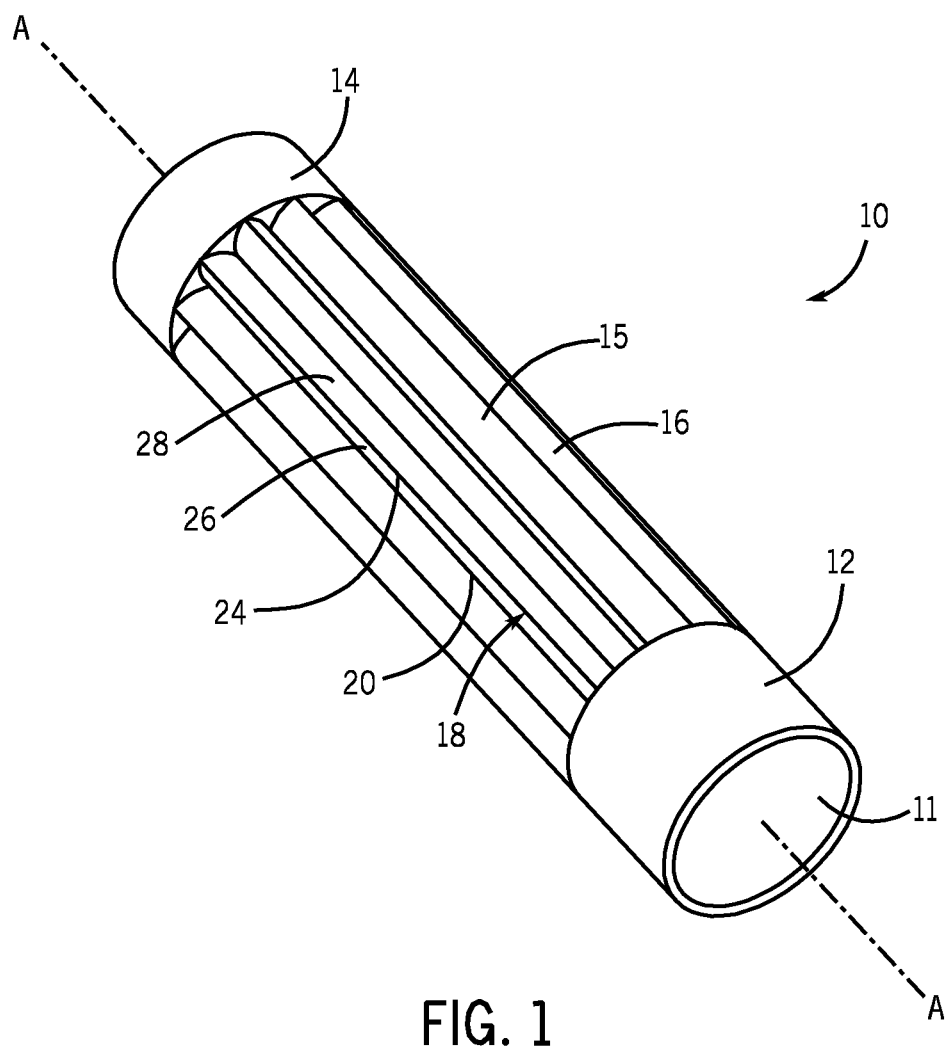
FIG. 1 is a perspective view of a breathing circuit tube in accordance with an embodiment.

Referring to FIG. 1, a perspective view of a tube 10 is shown tube in accordance with an embodiment. The tube 10 will hereinafter be described as a breathing circuit tube for use with healthcare devices such as respiratory or anesthesia machines. It should be appreciated, however, that other types of fluid tubes may be envisioned. It should be further appreciated that other types of tubes may be envisioned. For example, a tube directing a solid, such as cables and cords, may also be envisioned. The tube 10 comprises a first terminal end portion 12, a second terminal end portion 14, and a body 15. The tube 10 is preferably generally hollow and cylindrical in the absence of an externally applied force; however, other geometries are also envisioned. The tube 10 may define a passageway 11 and a central axis A-A therethrough. The tube 10 may comprise a flexible plastic or elastomeric material. It is also envisioned that the tube 10 may comprise a flexible or elastomeric material that comprises a spectrum of rigidity.

In the depicted embodiment the terminal ends portions 12, 14 define a non-corrugated region. The terminal end portions 12, 14 may comprise connectors of the type known in the art for facilitating interconnection of the tube 10 to medical devices or other apparatus (not shown), and the patient (not shown). The terminal end portions 12, 14 are preferably generally hollow and cylindrical in geometry; however, other geometries are also envisioned. For example, the terminal end portions may have a tapered cylindrical geometry wherein the first and second ends of the terminal end portions have different diameters. The terminal end portions 12, 14 may also comprise a flexible plastic or elastomeric material.

The body 15 is defined between the first and second terminal end portions 12, 14. The body 15 extends longitudinally along and parallel to the axis A-A and is hollow to direct a fluid flow between a medical device and a patient.

For purposes of this disclosure the term fluid should be defined to include any substance that continually deforms under an applied shear stress and may therefore include both liquids and gases. It is also envisioned that the tube 10 may direct solid objects, such as cables or cords. The body 15 is defined by a wall 16.

The wall 16 defines a generally hollow cylindrical geometry and is symmetric about the central axis A-A. The wall 16 forms the radial outermost perimeter of the passageway 11. The wall 16 defines a plurality of corrugations 18. It should be appreciated however, that the wall 16 may also define a single corrugation 18. For purposes of this disclosure, the term corrugation should be defined to include an expandable and contractible geometry similar to that of an accordion comprising a plurality of generally parallel and alternating folds. The parallel and alternating folds define a corresponding plurality of parallel and alternating crests 24 and troughs 20.

The corrugations 18 are spaced radially around the wall 16 and extend longitudinally along and parallel to the axis A-A. A single corrugation 18 comprises the generally v-shaped segment of wall 16 extending between two adjacent troughs 20. It is also envisioned that the corrugations 18 may comprise other geometries, for example sinusoid. Each corrugation 18 includes a crest 24, a first leg 26 disposed on one side of the crest 24, and a second leg 28 disposed on the opposite side of the crest 24. The troughs 20, crests 24 and legs 26, 28 extend longitudinally along and parallel to the axis A-A. For purposes of this disclosure, corrugations should be defined to be parallel with an axis (e.g., axis A-A) if the corrugation troughs, crests and/or legs are generally parallel with the axis. Similarly, corrugations should be defined to be perpendicular with an axis if the corrugation troughs, crests and/or legs are generally perpendicular with the axis. In the depicted embodiment, the corrugations 18 are spaced radially and evenly around the wall 16, however it is also envisioned that the corrugations 18 may be placed close together in clusters radially around the wall 16 with non-corrugated section of the wall 16 extending therebetween.

In the depicted embodiment, corrugations 18 extend longitudinally along the entire length of the wall 16. According to one alternative embodiment, the corrugations 18 may extend longitudinally along only a portion of the wall 16. According to another alternative embodiment, the wall 16 comprises radial corrugations 18 placed in sections along the axis of wall 16 longitudinally interspersed with sections of non-corrugated wall.

As previously described, the corrugations 18 are expandable and contractible. For purposes of this disclosure, a contracted corrugation 18 should be defined to be one in which the corrugation legs 26 are drawn together or nearly together. Similarly, an expanded corrugation 18 should be defined to be one in which the corrugation legs 26 are spread apart. It should be appreciated that the expansion and contraction of the corrugations 18 has the effect of adjusting the geometry defined by the wall 16.

Figure 2:
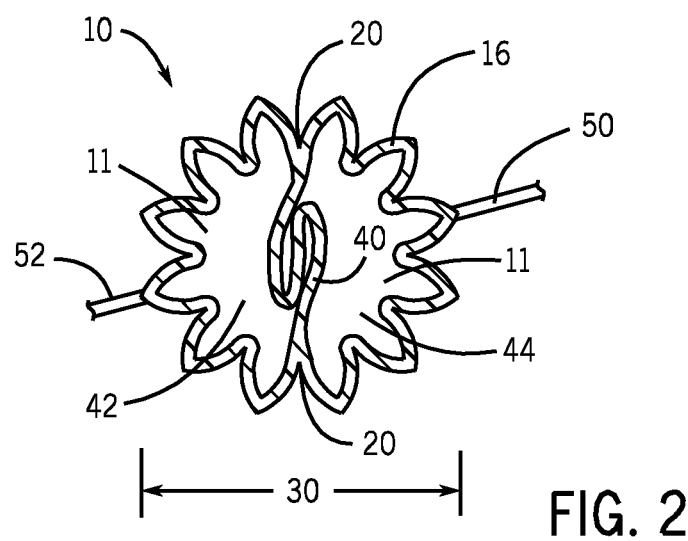
FIG. 2 is a cross-sectional view of a breathing circuit tube in accordance with an embodiment in a contracted state.
Figure 3:
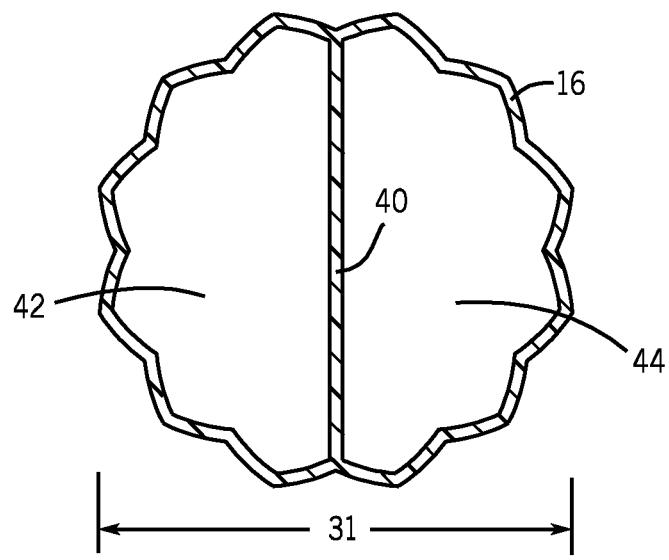
FIG. 3 is a cross-sectional view of a breathing circuit tube in accordance with an embodiment in an expanded state.

Referring to FIGS. 2 and 3, a cross-sectional view of the wall 16 is shown in a contracted and expanded state, respectively. In its contracted state depicted in FIG. 2, the wall 16 has an outer diameter 30. In its expanded state depicted in FIG. 3, the wall 16 has an outer diameter 31. It can be seen that the outer diameter 31 of the wall 16 in its expanded state greatly exceeds the outer diameter 30 of the wall 16 in its contracted state.

The expansion of wall 16 can be accomplished in a variety of ways. For example, as depicted in FIG. 2, tube 10 may further comprise opposed handles 50 and 52 that allow a user to exert opposing outward force to expand the wall 16. In another embodiment, the wall 16 may be expanded with the aid of a mandrel or die (not shown) having a selectable diameter in order set the diameter of the tube 10 at a predetermined value. In yet another embodiment, a pressure differential may be used to expand the tube 10 from its contracted state to its expanded state.

The expansion and contraction of the tube 10 is beneficial in procedures where both high and low fluid flow rates are required, as the tube 10 does not have to be disengaged from the medical device and substituted for a tube of a different diameter, but instead can simply be expanded or contracted to achieve a desired diameter. Similarly, the tube 10 could also be used to modify flow dynamics, for example, to increase flow speed in a longer circuit the diameter 30 could be reduced by contracting the corrugations 18 thus also passively reducing the efforts of the associated medical device. Additionally, a diametrically expandable and contractible tube may also reduce the healthcare provider's inventory as one product may be functional in neonate, pediatric and adult circuit sizes. This is an especially important attribute in countries where the expense of maintaining a wide inventory is problematic.

Referring now to FIG. 2, the tube 10 is shown comprising an optional partition 40. The partition 40 may be secured to and extend radially between generally opposite troughs 20 of the wall 16. The partition 40 may extend longitudinally along axis A-A and thereby divide the passageway 11 into a plurality of lumen 42 and 44. The partition 40 is preferably comprised of a flexible material such as, for example, a plastic or elastomer. When the wall 16 is in its contracted state depicted in FIG. 2, the partition 40 is appreciably folded over itself along the length of the tube 10 defining an S-shaped geometry. When the wall 16 is in its expanded state depicted in FIG. 3, the partition 40 is stretched so that it is no longer folded over itself but instead is substantially planar. It should be appreciated, however, that other types of partitions may be envisioned. For example, it is also envisioned that the partition 40 may comprise a stretchable and contractible material so that in the contracted state the partition 40 is planar in geometry (not shown), and the partition 40 stretches in its planar state when the wall 16 is in the expanded state. Alternatively, it is envisioned that the partition may comprise two opposing J-shaped hooks that mate or engage as described below in reference to FIGS. 7 and 8, thereby creating a plurality of lumen.

FIGS. 2 and 3 will now be described in accordance with an illustrative embodiment in which the tube 10 couples a patient (not shown) with a ventilator (not shown). In either the contracted or expanded state of the wall 16, breathing gases are transferred from the ventilator through a first lumen (e.g., lumen 42) and are then delivered into the patient's lungs. After the breathing gases are delivered into the patient's lungs, the patient passively exhales due to the elasticity of his or her lungs. The exhaled gas from the patient's lungs is transferred through another lumen (e.g., lumen 44) and is then vented to atmosphere or a collection system (not shown).

While the embodiment depicted in FIGS. 2 and 3 comprises a single partition and two lumen, it should be appreciated, however, that the passageway 11 may comprise more than one partition. For example, a passageway comprising two partitions and three lumens may be beneficial for gas sampling purposes, or for accommodating the flow of forced hot air adjacent to the inspiratory lumen.

Figure 4:
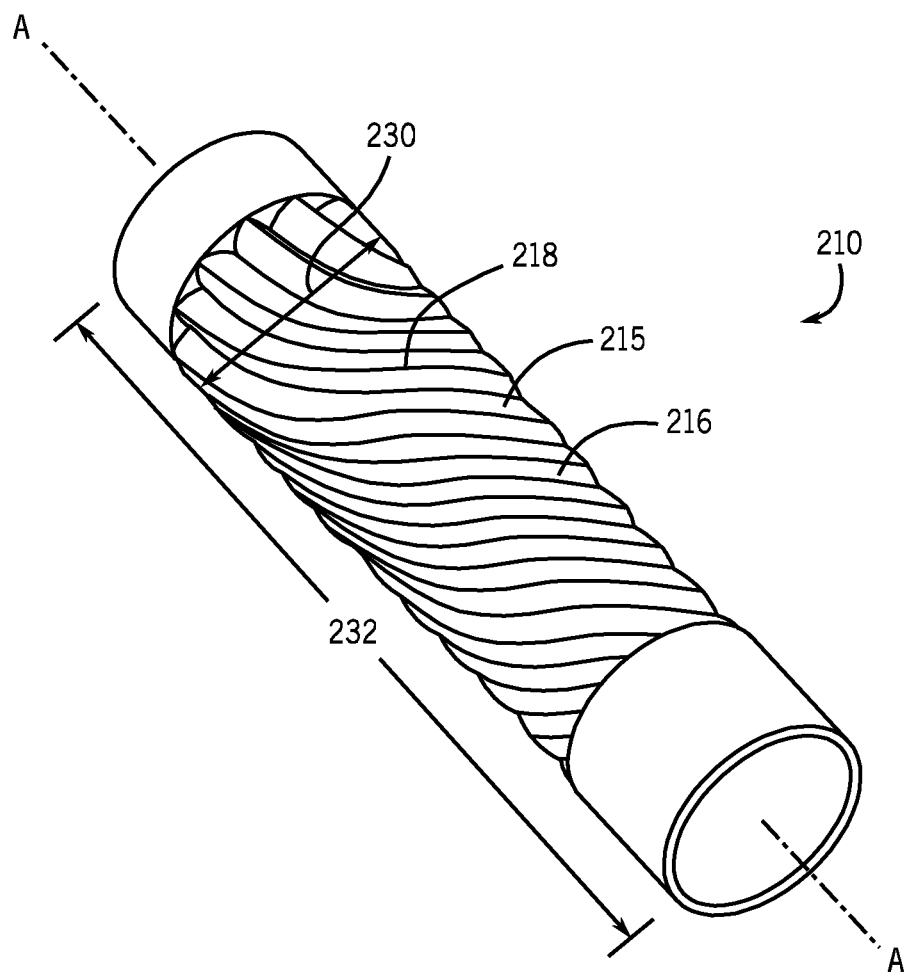
FIG. 4 is a perspective view of a breathing circuit tube in accordance with an alternate embodiment of the present invention wherein the corrugations have been configured in a helical fashion.

Referring to FIG. 4, a breathing circuit tube 210 is shown in accordance with an alternate embodiment. The tube 210 comprises a body 215 defining a wall 216 with a plurality a helical corrugations 218, but is otherwise similar to the tube 10. The corrugations 218 are spaced radially around wall 216 and define a generally helical geometry about axis A-A. The corrugations 218 are both expandable and contractible in a manner similar to that previously described with respect to the corrugations 18 (shown in FIG. 1). The helical geometry of the corrugations 218 allows for adjustments to both the diameter 230 and length 232 of the tube 210 as the corrugations 218 are expanded or contracted.

Figure 5:
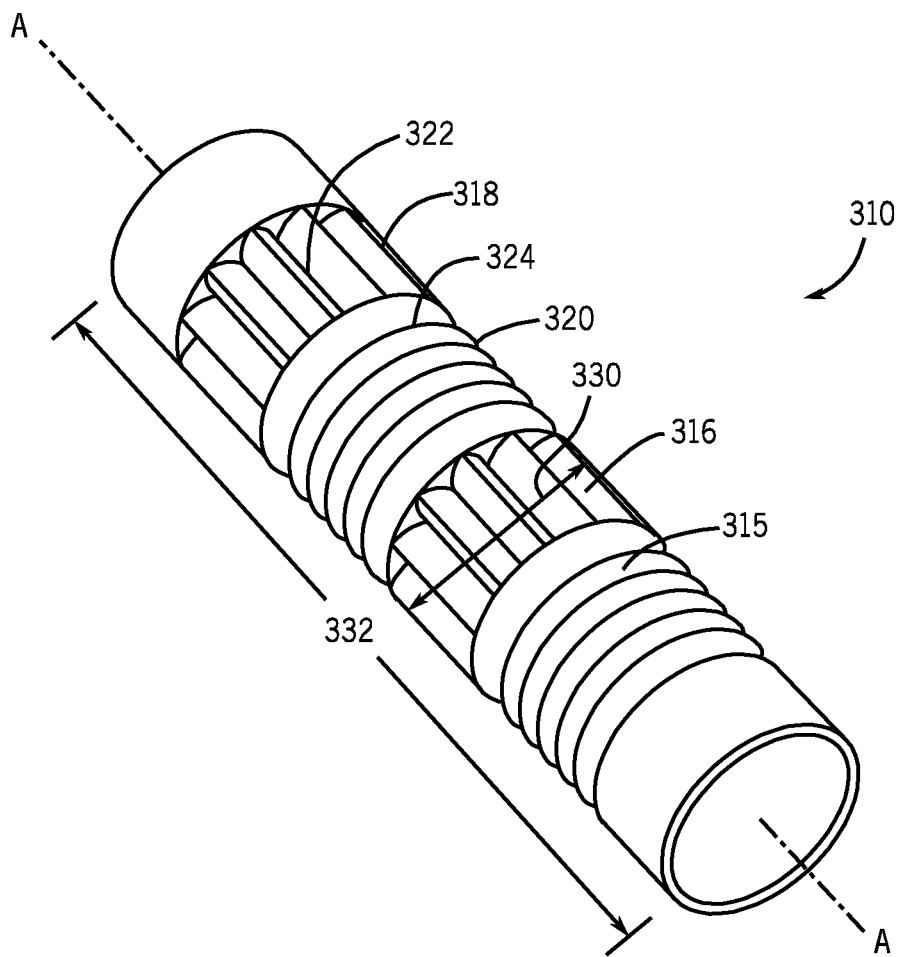
FIG. 5 is a perspective view of a breathing circuit tube in accordance with an alternate embodiment of the present invention wherein the corrugations have been configured into alternate radial corrugation and axial corrugation sections.

Referring to FIG. 5, a breathing circuit tube 310 is shown in accordance with another alternate embodiment. The tube 310 comprises a body 315 defined by a hollow cylindrical wall 316 with a plurality of alternately aligned corrugated sections 318 and 320 extending longitudinally along the length of the tube 310, but is otherwise similar to the tube 10. At least one corrugated section 318 comprises radial corrugations 322 while the alternate corrugated section 320 comprises axial corrugations 324. The radial corrugations 322 extend longitudinally along and parallel to axis A-A and allow for expansion and contraction of the diameter 330 of tube 310. The axial corrugations 324 are perpendicular to and axial about axis A-A, and allow for expansion and contraction of the length 332 of the tube 310. Such axial corrugations 324 are commonly known in the art. The alternating geometry of the corrugated sections 318, 320 allows for adjustments to both the diameter and length of the tube 310 as the corrugated sections 318, 320 are expanded and contracted. It should be appreciated that other combinations of corrugated sections are envisioned. For example, a breathing circuit tube may comprise a combination of radial, axial or helical corrugated sections.

A tube 310 comprising a combination of radial and axial corrugated sections 318 and 320 provides several benefits including flexibility in draping and positioning, and the deterrence of kinking and obstruction of gas flow in the tube. Additionally, the tube 310 may provide a mechanism for reducing condensation or other fluid within the breathing circuit. For example, diameter changes may affect pressure drops that may lead to moisture staying in the air flow rather than condensing into droplets.

Figure 6:
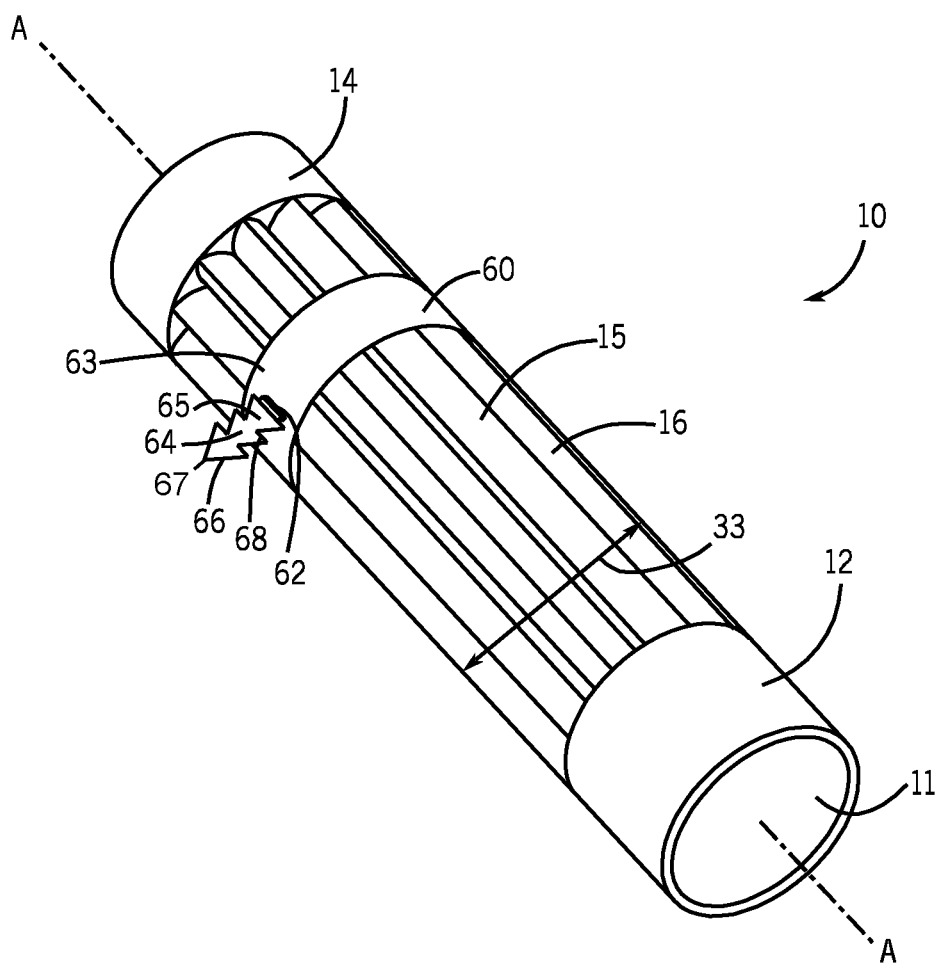
FIG. 6 is a perspective view of a breathing circuit tube in accordance with an embodiment of the present invention.

Referring to FIG. 6, a breathing circuit tube 10 comprises an optional strap 60. The strap 60 is preferably a zip tie as is commonly known in the art, but may also be any other kind of device that can be fastened about the body 15 to limit the diameter 33 of the body 15 to a selectable value. In the depicted embodiment, the strap 60 comprises an insertion point 62 on a first end 63 and a sequentially tapered region 64 on an opposing end 65. When the strap 60 is utilized, a user may wrap the strap 60 around the circumference of body 15 and set a fixed maximum diameter 33 by inserting a pointed tip 67 through the insertion point 62 by a selectable amount and thereby fastening the strap 60 about the body 15.

Selecting the fixed maximum diameter 33 may be accomplished in a variety of ways. The strap 60 may comprise a single insertion point 62. The sequentially tapered region 64 may define a plurality of tapered sections 66 and a corresponding plurality of under-cut shoulders 68. Once the tapered region 64 of the strap has been pulled through the insertion point 62 and past the first tapered section 66, it is prevented from being pulled back out of the insertion point 62 by a corresponding under-cut shoulder 68. To further tighten the strap 60, thereby decreasing the potential maximum diameter 33, the user may increase the degree to which the tapered region 64 is inserted through the insertion point 62. Alternatively, the strap 60 may also comprise a plurality of insertion points (not shown) designed to set the diameter 33 of the tube 10 for treatment of a neonate, a pediatric patient or an adult patient. It should also be appreciated that other methods for selecting a fixed diameter are envisioned. For example, a flexible clip of circular or other geometry may be inserted into the passageway.

Figure 7:
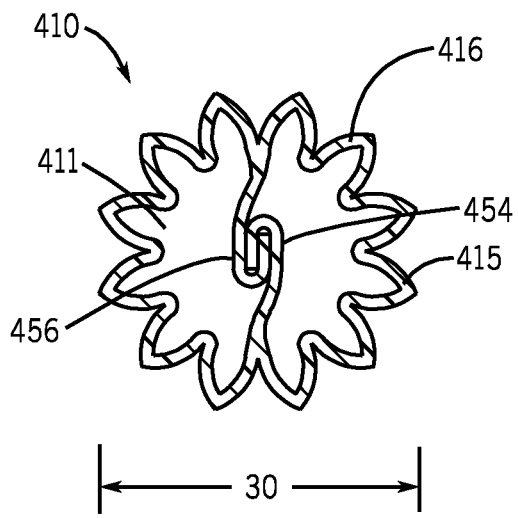
FIG. 7 is a cross-sectional view of a breathing circuit tube in accordance with an alternate embodiment in a contracted state.
Figure 8:
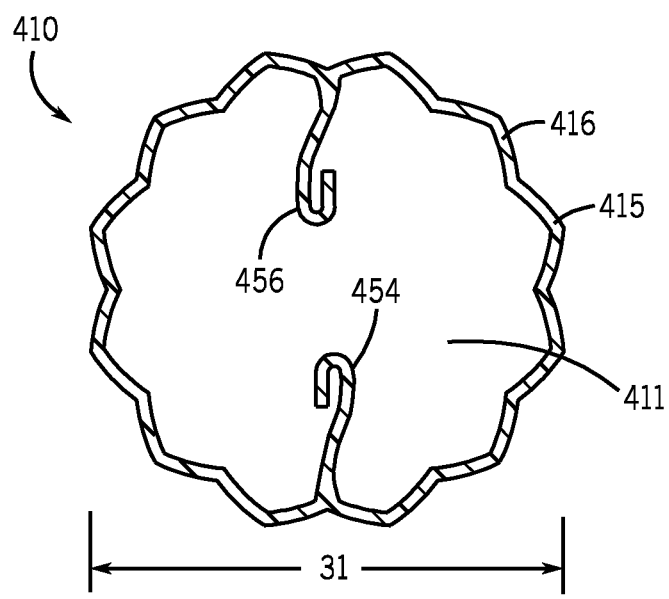
FIG. 8 is a cross-sectional view of a breathing circuit tube in accordance with an alternate embodiment in an expanded state.

Referring to FIGS. 7 and 8, a breathing circuit tube 410 is shown in accordance with another alternate embodiment wherein the tube 410 is shown in the contracted and expanded states respectively. The tube 410 comprises a body 415 defined by a hollow cylindrical wall 416. The wall 416 forms the radial outermost perimeter of the passageway 411. The tube 410 further comprises opposing hooks 454, 456 ending into the passageway 411. The opposing hooks 454, 456 are preferably "J-shaped" but may also be shaped in other ways that allow the hooks 454, 456 to hold the tube 410 in a contracted state when mating or engaged, and when the hooks 454, 456 are not mating allow the tube 410 to expand. To mate the hooks 454, 456, a user may exert external opposing compressing force on the tube 410 so that the hooks 454, 456 slide past one another and mate or engage.

Alternatively, the tube may comprise opposing members extending into the passageway. The first member comprises a J-shaped hook while the second member comprises one or more barbs along its length. The hook of the first member is then able to engage with a barb of the second member and lock in place, thereby contracting the diameter of the passageway. It should be appreciated that alternative geometries are envisioned for the first and second members. For example, the first member may have a kick-stand, or pointed geometry and be able to engage with the barbs to prop the passageway open at a fixed diameter.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A fluid tube comprising:
    a wall comprising a hollow geometry defining a passageway with a central longitudinal axis therethrough, the wall defining a diameter and a length of the passageway, the wall being expandable and contractible to adjust the diameter, the wall being expandable and contractible to adjust the length; and
    a component configured to restrict expansion or contraction of the wall.

2. The fluid tube of claim 1, wherein the component comprises an adjustable strap around a circumference of the wall and configured to set a fixed diameter of the passageway.

3. The fluid tube of claim 1, wherein the component comprises a flexible clip inserted into the passageway.

4. The fluid tube of claim 1, wherein the component comprises a first member and a second member, the first member configured to mate with the second member to hold the wall in a contracted state.

5. The fluid tube of claim 4, wherein the first member comprises a J-shaped hook.

6. The fluid tube of claim 5, wherein the second member comprises a J-shaped hook.

7. The fluid tube of claim 5, wherein the second member comprises a barb.

8. The fluid tube of claim 1, wherein the component comprises a first member having a pointed geometry and a second member comprising a barb, and wherein the first member is configured to engage the second member to prop the passageway open at a fixed diameter.

9. A fluid tube comprising:
a wall comprising a hollow geometry defining a passageway with a central longitudinal axis therethrough, the wall defining a diameter and a length of the passageway, the wall comprising a first plurality of corrugations and a second plurality of corrugations, the first plurality of corrugations expandable and contractible to adjust the diameter, the second plurality of corrugations expandable and contractible to adjust the length; and
a component configured to restrict expansion or contraction of the wall.

10. The fluid tube of claim 9, wherein the component comprises an adjustable strap around a circumference of the wall and configured to set a fixed diameter of the passageway.

11. The fluid tube of claim 9, wherein the component comprises a flexible clip inserted into the passageway.

12. The fluid tube of claim 9, wherein the component comprises a first member and a second member, the first member configured to mate with the second member to hold the wall in a contracted state.

13. The fluid tube of claim 12, wherein the first member comprises a J-shaped hook.

14. The fluid tube of claim 13, wherein the second member comprises a J-shaped hook.

15. The fluid tube of claim 13, wherein the second member comprises a barb.

16. The fluid tube of claim 9, wherein the component comprises a first member having a pointed geometry and a second member comprising a barb, and wherein the first member is configured to engage the second member to prop the passageway open at a fixed diameter.

17. A fluid tube comprising:
a wall comprising a hollow geometry defining a passageway with a central longitudinal axis therethrough, the wall defining a diameter and a length of the passageway, the wall comprising a plurality of corrugations, the plurality of corrugations expandable and contractible to adjust the diameter and the length; and
a component configured to restrict expansion or contraction of the wall.

18. The fluid tube of claim 9, wherein the component comprises an adjustable strap around a circumference of the wall and configured to set a fixed diameter of the passageway.

19. The fluid tube of claim 9, wherein the component comprises a flexible clip inserted into the passageway.

20. The fluid tube of claim 9, wherein the component comprises a first member and a second member, the first member configured to mate with the second member to hold the wall in a contracted state.

* * * * *